United States Patent [19]
Koichiro et al.

[11] Patent Number: 4,780,313
[45] Date of Patent: Oct. 25, 1988

[54] METHOD OF STIMULATING THE IMMUNE SYSTEM WITH A MIXTURE OF SUBSTANCES HAVING IL-2 ACTIVITY AND MURAMYLDIPEPTIDE

[75] Inventors: Ootsu Koichiro, Mishima; Goto Giichi, Toyono, both of Japan

[73] Assignee: Takeda Chemical Industries, Ltd., Osaka, Japan

[21] Appl. No.: 943,924

[22] Filed: Dec. 18, 1986

[30] Foreign Application Priority Data

Dec. 24, 1985 [JP] Japan ................................. 60-291471

[51] Int. Cl.$^4$ ...................... A61K 37/02; A61K 39/39
[52] U.S. Cl. ........................................... 424/88; 514/2; 514/8; 514/885; 530/351
[58] Field of Search ................. 424/88; 514/2, 8, 885; 530/351

[56] References Cited

U.S. PATENT DOCUMENTS

| | | | |
|---|---|---|---|
| 4,369,178 | 1/1983 | Yamamura et al. | 530/300 |
| 4,401,659 | 8/1983 | Lefrancier et al. | 530/395 |
| 4,518,584 | 5/1985 | Mark | 435/68 |
| 4,639,512 | 1/1987 | Audibert et al. | 424/88 |

FOREIGN PATENT DOCUMENTS 89062  9/1983  European Pat. Off. .

OTHER PUBLICATIONS

J. Immunol. 125, 1904 (1980).
Souvannavong et al, *Biochem. Biophys. Res. Comm.*, 125(1) 1984, pp. 431–439.
Souvannavong et al, *Biochem. Biophys. Res. Comm.*, 114(2) 1983, pp. 721–728.
Dinarello et al, *Fel. Proc.* 45, 1986, pp. 2545–2548.
Nitta et al, *Microbiol. Immunol.* 29(5) 1985, pp. 441–449 (CA 103 #86307k).
Guenounou et al, *Comp. Immunol. Microbiol. Infert. Dis.*, 8(3-4) 1985 pp. 273–284 (Biosis abstract).
Kishter et al, *J. Biol. Resp. Modif.*, 4(2) 1985 (Biosis abstract only) pp. 185–194.
Fidler et al, Site Specific Drug Delivery, ed Tomlinson et al, 1982, page (varies).

Primary Examiner—John Kight
Assistant Examiner—Garnette D. Draper
Attorney, Agent, or Firm—David G. Conlin; Ronald I. Eisenstein

[57] ABSTRACT

The combined use of an IL-2-active substance with a muramyldipeptide exhibiting a remarkably potent immunostimulant activity than the single use of the active ingredient is disclosed.

11 Claims, 1 Drawing Sheet

Fig. 1

```
1
Ala Pro Thr Ser Ser Ser Thr Lys Lys Thr Gln Leu Gln
                              20
Leu Glu His Leu Leu Leu Asp Leu Gln Met Ile Leu Asn

Gly Ile Asn Asn Tyr Lys Asn Pro Lys Leu Thr Arg Met
40
Leu Thr Phe Lys Phe Tyr Met Pro Lys Lys Ala Thr Glu
                              60
Leu Lys His Leu Gln Cys Leu Glu Glu Glu Leu Lys Pro

Leu Glu Glu Val Leu Asn Leu Ala Gln Ser Lys Asn Phe
    80
His Leu Arg Pro Arg Asp Leu Ile Ser Asn Ile Asn Val
                              100
Ile Val Leu Glu Leu Lys Gly Ser Glu Thr Thr Phe Met

Cys Glu Tyr Ala Asp Glu Thr Ala Thr Ile Val Glu Phe
            120
Leu Asn Arg Trp Ile Thr Phe Cys Gln Ser Ile Ile Ser
            133
Thr Leu Thr
```

METHOD OF STIMULATING THE IMMUNE SYSTEM WITH A MIXTURE OF SUBSTANCES HAVING IL-2 ACTIVITY AND MURAMYLDIPEPTIDE

The present invention relates to an immunostimulant agent.

Attempts have been made in recent years, develop immunostimulant agent against various viral infections by using lymphokines such as interleukin-2 for immunopotentiation [J. Immunol., 125, 1904 (1980)]. The above-mentioned interleukin-2, which is a macromolecular protein, has become producible in high purity and in large quantities and at relatively low cost by the use of genetic engineering techniques (Japanese Patent Laid-open No. 60-115528 which corresponds to EPC Publication No. 145390).

It is also known that N-acetylmuramyl-L-alanyl-D-isoglutamine, which is included among the class of muramyldipeptides, is synthesized as a minimum structural unit necessary for the expression of bacterial cell wall adjuvant activity, and furthermore, various muramyldipeptides have been synthesized. They exhibit potent adjuvant activity, typically antitumor activity or macrophage activation activity (Immunobiology and Immunotherapy of Cancer, edited by Yamamura et al., pp. 311–330, Elsevier/North Holland, New York, 1979).

Single application of the above-mentioned interleukin-2 (IL-2) or muramyldipeptide including their use as immunostimutant agents have been made but so far no fully satisfactory results have been obtained.

Some means of enhancing the immunostimulant effect are known, for instance to increase the dose of the above-mentioned medicinal substances. However, high dosage treatment is generally unsatisfactory due to manifestation of various adverse effects such as pyrexia, headache and exanthema.

In the course of their endeavors to develop a way of using IL-2 as an immunostimulant agent, the present inventors have found that the use of IL-2 in combination with a muramyldipeptide results in a remarkably enhanced immunostimulant activity, which can not be produced by using only IL-2, and simultaneously can alleviate or prevent the above-mentioned adverse effects and the like. Further intensive study based on this finding has led to completion of the present invention.

The present invention is directed to:

(1) an immunostimulant agent which comprises a substance having interleukin-2 activity in combination with a muramyldipeptide and a pharmaceutically acceptable carrier;

(2) a method for immunostimulating a warm-blooded animal, which comprises administering a substance having interleukin-2 activity in combination with a muramyldipeptide to said animal; and (3) a substance having interleukin-2 activity in combination with a muramyldipeptide, for use in the treatment of immunostimulating a warm-blooded animal.

The substance having interleukin-2 (IL-2) activity as mentioned above may be any substance having IL-2 activity, namely activity to allow indefinite propagation of T cells by continuous culture in vitro without altering their function.

This substance would include natural IL-2 produced in animal bodies or in animal cells or genetically engineered IL-2, or a substance related thereto. The above-mentioned IL-2 or related substance, when it is a protein, may have or not have a sugar chain.

More specifically, it may be, for example, Polypeptide (A) [see EPC Publication No. 176299] which is produced using genetic engineering techniques and which has the amino acid sequence in FIG. 1, and its fragments having a sufficient amino acid sequence essential to its biological or immunological activity.

The recombinant human IL-2, for example, includes a fragment lacking one amino acid from Polypeptide (A) at the amino terminus (EPC Patent Publication No. 91539), a fragment lacking four amino acids from Polypeptide (A) at the amino terminus (Japanese Patent Laid-open No. 60-126088), and fragments lacking several amino acids from Polypeptide (A) at the carboxy terminus.

Furthermore, as the recombinant human IL-2, there are also included polypeptides produced by the elimination or substitution of other amino acids, as in the case of some constitutional amino acids in the above-mentioned Polypeptide (A), e.g. a polypeptide produced by replacing the cysteine residue at the 125th position with a serine residue in Polypeptide (A) (Japanese Patent Laid-open No. 59-93093 which corresponds to U.S. Pat. No. 4,518,584).

The above-mentioned IL-2 may be chemically modified, for example with a polyethylene glycol derivative (e.g. Japanese Patent Laid-open No. 60-226821).

In the practice of the invention, human IL-2 which has the amino acid sequence shown in FIG. 1 is most preferably used. In that case, it may be a mixture of one further having a methionine residue (Met) at the amino terminus thereof and one not having the Met residue (Japanese Patent Laid-open No. 60-115528 which corresponds to EPC Publication No. 145390). The latter polypeptide having no Met at the amino terminus but starting with alanine (Ala) (Japanese Patent Application No. 60-205873 which corresponds to EPC Publication No. 176299) is preferred.

As the substance having interleukin-2 activity, a recombinant non-glycosylated human interleukin-2 is preferred.

The muramyldipeptide includes compounds of the formula (I)

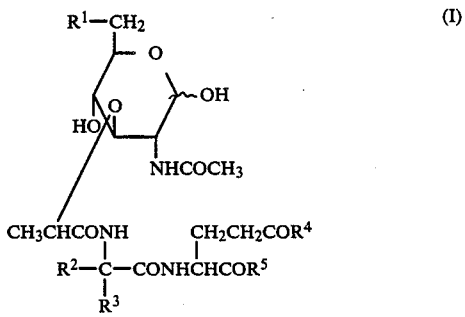

wherein $R^1$ is a hydroxyl group or a carboxylic acid residue, $R^2$ and $R^3$ each independently is hydrogen or a lower ($C_{1-6}$) alkyl group, which may optionally be substituted by a hydroxyl group, $R^4$ is a hydroxyl group or a lower ($C_{1-6}$) alkoxy group and $R^5$ is a hydroxyl group or a substituted or unsubstituted amino group, and physiologically acceptable salts thereof.

Compounds of formula (I) and salts thereof are known compounds and are described in U.S. Pat. No. 4,101,536, Japanese Patent Laid-open No. 54-63016, Japanese Patent Laid-open No. 54-79228 (which corresponds to EPC Publication No. 2677) and Japanese Patent Laid-open No. 55-111499 (which corresponds to U.S. Pat. No. 4,369,178), for instance.

Thus, in referring to compounds of the formula (I), the carboxylic acid residue represented by $R^1$ is, for example, mycoloyl, stearoyl, oleoyl or a $C_2$–$C_{50}$ carboxylic acid residue of the formula (II)

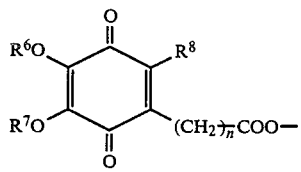

wherein $R^6$, $R^7$ and $R^8$ each independently is a lower ($C_{1-4}$) alkyl and n is an integer of 1 to 10, inclusive. Such carboxylic acid residue may further contain an intervening amino acid residue such as a glycine, alanine or β-alanine residue. The lower alkyl group represented by $R^2$ and/or $R^3$ is preferably a $C_1$–$C_4$ alkyl, for example methyl, ethyl, propyl, isopropyl, butyl, isobutyl, sec-butyl or t-butyl. When substituted by a hydroxyl group, such lower alkyl can be hydroxymethyl or 2-hydroxymethyl, for instance.

The lower alkoxy represented by $R^4$ is preferably a $C_1$–$C_3$ alkoxy, namely methoxy, ethoxy, propoxy or isopropoxy. The hydroxyl group represented by $R^4$ may have a hapten-active substituent such as an ester residue of N-hydroxy-2-norbornene-2,3-dicarboxyimide.

The substituted or unsubstituted amino group represented by $R^5$ is a primary amino group or an amino group having one or two substituents. Examples of said substituents are lower ($C_1$–$C_3$) alkyl (e.g. methyl, ethyl, propyl, isopropyl, etc.), phenyl, and aralkyl (e.g. benzyl, phenethyl, etc.).

Preferably the muramyldipeptide in the compounds of the formula (I), in which $R^1$ is a hydroxyl group or a $C_2$–$C_{50}$ carboxylic acid residue of the formula (II) wherein $R^6$, $R^7$ and $R^8$ each independently is a lower ($C_{1-4}$) alkyl and n is an integer of 1 to 10, $R^2$ and $R^3$ is hydrogen or a lower ($C_{1-6}$) alkyl group which may optionally be substituted by a hydroxyl group, $R^4$ is a hydroxyl group or a lower ($C_{1-6}$) alkoxy group, and $R^5$ is a hydroxyl group or an amino group.

Typical examples of the muramyldipeptide of the above formula (I) are muramyldipeptide mycolic acid esters (e.g. 6-0-mycomycoloyl-N-acetylmuramyl-L-alanyl-D-isoglutamine, 6-0-mycomycoloyl-N-acetylmuramyl-L-seryl-D-isoglutamine, 6-0-nocardomycoloyl-N-acetylmuramyl-L-seryl-D-isoglutamine, 6-0-ursomycoloyl-N-acetylmuramyl-L-seryl-D-isoglutamine), muramyldipeptide fatty acid esters (e.g. 6-0-stearoyl-N-acetylmuramyl-L-alanyl-D-isoglutamine, 6-0-stearoyl-N-acetylmuramyl-L-seryl-D-isoglutamine, 6-0-oleoyl-N-acetylmuramyl-L-alanyl-D-isoglutamine), muramyldipeptide quinonylalkanoic acid esters (e.g. 6-0-[3-(2,3-dimethoxy-5-methyl-1,4-benzoquinon-6-yl)propionyl]-N-acetylmuramyl-L-valyl-D-isoglutamine, 6-0-[10-(2,3-dimethoxy-5-methyl-1,4-benzoquinon-6-yl)decanoyl]-N-acetylmuramyl-L-valyl-D-isoglutamine, 6-0-[10-(2,3-dimethoxy-5-methyl-1,4-benzoquinon-6-yl)decanoyl]-N-acetylmuramyl-L-seryl-D-isoglutamine), muramyldipeptides (e.g. N-acetylmuramyl-L-alanyl-D-isoglutamine (abbreviated as TMD-1)), N-acetylmuramylaminoisobutyryl-D-isoglutamine (abbreviated as TMD-5) and lower alkyl esters in the isoglutamine moiety of the above compounds (e.g. 6-0-[3-(2,3-dimethoxy-5-methyl-1,4-benzoquinon-6-yl)propionyl]-N-acetylmuramyl-L-valyl-D-isoglutamine methyl ester (abbreviated as TMD-76), 6-0-[10-(2,3-dimethoxy-5-methyl-1,4-benzoquinon-6-yl)decanoyl]-N-acetylmuramyl-L-valyl-D-isoglutamine methyl ester (abbreviated as quinonyl-MDP-66), 6-0-[10-(2,3-dimethoxy-5-methyl-1,4-benzoquinon-6-yl)decanoyl]-N-acetylmuramyl-L-seryl-D-isoglutamine methyl ester.

In the practice of the present invention, TMD-1, TMD-5, TMD-76, quinonyl-MDP-66 and similar water-soluble muramyldipeptides are particularly preferred among the above-mentioned muramyldipeptides.

The substance having IL-2 activity (IL-2 active substance) and the muramyldipeptide, which are to be used in accordance with the invention, have low toxicity, for example, the minimum lethal doses (MLDs) of IL-2 obtained by the manner of EPC Publication No. 145390 is not less than 10 mg/mouse (1 mg = $3.5 \times 10^4$ units/mg) (S.C.) and the minimum lethal doses (MLDs) for the muramyldipeptide is not less than 500 mg/kg (S.C.) in rats. Therefore, the substance having IL-2 activity and the muramyldipeptide can be used safely.

They are administered either orally or parenterally in doses dependent on the mode of use, purpose of use and other factors. The effective amount is desirably in a proportion of about 0.5 to 1,000 mcg, preferably about 50 to 400 mcg, of the muramyldipeptide per one mcg, as protein, of the IL-2-active substance (35 units (U) in terms of IL-2 activity; for the IL-2 activity assay, see Japanese Patent Laid-open No. 60-115528 which corresponds to EPC Publication No. 145390. One unit (U) corresponds to the IL-2 activity of 28.6 ng of pure recombinant IL-2). The dose of the immunostimulant agent according to the present invention may also vary depending on the kind of IL-2 or muramyldipeptide employed. Generally, the effective amount of the daily dose for a warm-blooded mammals (e.g. mouse, cat, dog, cattle, sheep, goat, rabbit, human) as expressed in terms of IL-2 protein weight is preferably about 0.1 to 500 mcg/kg for mouse and about 0.001 to 10 mcg/kg for mammals other than mouse, more preferably 0.001 to 4 mcg/kg for mammals other than mouse in a form of injections, about 0.01 to 20 mcg/kg in a form of suppositories, about 0.001 to 2 mcg/kg in a form of drip infusion preparations, about 0.2 to 40 mcg/kg in a form of preparation for percutaneous absorption.

The immunostimulant agent according to the present invention which comprises an IL-2-active substance in combination with a muramyldipeptide can be made up for administration by mixing the substance or substances according to an appropriate known pharmaceutical process, using, as desired, one or more pharmaceutically acceptable carriers (including diluents, excipients and the like.) It is also possible to make up the respective substances into separate preparations or combine these active substances at the time of use into a single preparation containing them for administration by using a diluent, for instance. It is further possible to administer the above separate preparations to the same subject either simultaneously or at a certain time interval.

When preparing an agent for injection, as the carrier, there are mentioned distilled water, physiological saline and human serum albumin-supplemented distilled water or physiological saline.

As the carrier for an agent for suppositories, there are mentioned disaturated triglycerides, hydrogenated triglycerides, gelatin, glycerin, polyethylene glycol monostearate etc.

As the carrier for an agent for drip infusion preparations, there are mentioned distilled water, physiological saline, dextran sulfate solution.

As the carrier for an agent for percutaneous absorption, several kinds of ointment bases such as glycerin, sodium lauryl sulfate, polyethylene glycol ointment, white wax etc. are usable.

The preparations of the present invention are made up in conventional manners employing the said carrier.

An example of the immunostimulant agent of the present invention includes an antitumor agent for treatment of a warm-blooded animal having one or more tumors.

The antitumor agent is useful in the treatment or prevention of tumor in the warm-blooded mammal and produces remarkable effects in prolonging the lifespan in tumor-bearing mammals, for instance. As such target diseases, there are various types of leukemia, malignant lymphoma, myeloma, malignant melanoma, malignant chorionic tumor, myoma, ovarian cancer, uterine cancer, prostatic cancer, spleen cancer, digestive organ cancer such as stomach cancer or intestinal cancer, lung cancer, esophageal cancer, cervicalcephalic cancer and cerebral tumor, among others.

The immunostimulant agent comprising an IL-2-active substance in combination with a muramyldipeptide in accordance with the present invention has potent immunostimulant activity which is not exhibited by sole use of each individual ingredient, and results in a substantial reduction in side effects.

which is obtained by the manner described in Example 5 of EPC Publication No. 176299 employing *Escherichia coli* N4830/pTB285 (IFO 14437, FERM BP-852).

EXAMPLES

Example 1

(Antitumor activity in the case of subcutaneous administration)

Meth-A fibrosarcoma cells (Meth-A tumor cells) ($1 \times 10^6$ cells) were transplanted into each female BALB/c mice (weighing about 20 g) subcutaneously in the flank using a syringe. Seven days after tumor transplantation, mice in which tumor was larger than a certain defined size were chosen and grouped and administration of the test agent was started. The agent was administered subcutaneously in the opposite flank relative to the tumor transplantation site once daily for 10 consecutive days. Each ingredient of the test agent was dissolved in physiological saline (solvent) supplemented in a form of a single preparation with 5% of normal mouse serum in a concentration such that the dose of the solution amounted to 0.1 ml/20 g of mouse body weight. The antitumor effect was evaluated by measuring the tumor weight in each mouse 21 days after tumor transplantation, determining the average tumor weight for each group and calculating the tumor weight ratio (T/C %) between the dosed group (T; 5 animals per group) and the untreated control group (C; 5 to 10 animals per group). The daily dose of each ingredients was expressed in terms of the ingredient weight (mcg) per mouse. The results of single administration of IL-2 and those of administration of antitumor agents comprising IL-2 and N-acetylmuramyl-L-alanyl-D-isoglutamine (TMD-1) in accordance with the invention are shown in Table 1.

TABLE 1

| Experiment No. | Dose (mcg/mouse/day) IL-2 | Dose (mcg/mouse/day) TMD-1 | Number of animals | Tumor weight (mg) Mean ± SD | Tumor weight ratio (T/C %) | Body weight gain (g) (day 7 to day 21) |
|---|---|---|---|---|---|---|
| I | Untreated control | | 9* | 4,836 ± 996 | | 2.5 |
| | Solvent (control) | | 5 | 6,537 ± 595 | 135 | 3.6 |
| | 0 | 200 | 5 | 2,995 ± 846 | 62 | 1.3 |
| | 10 | 0 | 5 | 2,359 ± 1,064 | 49 | 1.0 |
| | 1 | 200 | 5 | 2,548 ± 1,037 | 53 | 0.9 |
| | 10 | 200 | 5 | 375 ± 504 | 9 | −0.2 |
| II | Untreated control | | 5 | 7,035 ± 1,201 | | 4.7 |
| | Solvent (control) | | 5 | 5,717 ± 2,060 | 81 | 3.0 |
| | 10 | 0 | 5 | 2,605 ± 709 | 37 | 1.4 |
| | 10 | 200 | 5 | 866 ± 622 | 12 | 0.4 |
| | 10 | 400 | 5 | 485 ± 479 | 7 | 0.5 |

*The test was started with 10 animals in this group but one animal died from tumor the day before autopsy.

BRIEF DESCRIPTION OF THE DRAWINGS

FIG. 1 shows an example of a preferred embodiment of the amino acid sequence of IL-2 to be used in the practice of the present invention.

The following Examples are further illustrative of the working and mode of practice of the present invention but are by no means limitative thereof.

The IL-2 employed in the following Examples 1 to 7 is a genetically engineered IL-2 species employing *Escherichia coli* DH1/pTF4 (IFO 14299, FERM BP-628) prepared by the manner described in Japanese Patent Laid-open No. 60-115528 (EPC Publication No. 145390).

The "Ala-species" of IL-2 employed in the following Examples 8 to 10 is a genetically engineered IL-2 species whose amino terminus amino acid is Ala-Pro-,

Example 2

(Antitumor activity in the case of intravenous administration)

Meth-A tumor cells ($1 \times 10^6$ cells) were transplanted into each female BALB/c mice (weighting about 20 g) subcutaneously in the flank with a syringe. Seven days after tumor transplantation, mice in which tumor was larger than a certain defined size were chosen and grouped and administration of the test agent was started. The agent was administered via the caudal vein once daily for 10 consecutive days. Each ingredient of the test agent was dissolved in physiological saline (solvent) in the form of a single preparation supplemental with 5% of normal mouse serum in a concentration such that the dose of the solution amounted to 0.2 ml/20 g of mouse body weight. The antitumor effect was evaluated by measuring the tumor weight in each animal 21 days after tumor transplantation, determining the average tumor weight for each group and calculating the tumor weight ratio (T/C%) between the dosed group (T; 5 animals per group) and the untreated control group (C; 10 animals). The results of single administration of IL-2 and those of administration of antitumor agents comprising IL-2 and N-acetylmuramyl-L-alanyl-D-isoglutamine (TMD-1) in accordance with the invention are shown in Table 2. The daily dose of each ingredient was expressed in terms of the ingredient weight (mcg) per mouse.

TABLE 2

| Dose (mcg/mouse/day) | | Number of animals | Tumor weight (mg) Mean ± SD | Tumor weight ratio (T/C %) | Body weight gain (g) (day 7 to day 21) |
| --- | --- | --- | --- | --- | --- |
| IL-2 | TMD-1 | | | | |
| Untreated control | | 9* | 6,890 ± 1,150 | | 4.3 |
| Solvent (control) | | 5 | 5,315 ± 1,439 | 77 | 3.7 |
| 10 | 0 | 5 | 4,368 ± 959 | 63 | 2.9 |
| 10 | 200 | 5 | 2,226 ± 1,002 | 32 | 1.5 |
| 10 | 400 | 5 | 1,390 ± 1,429 | 20 | 0.9 |

*The test was started with 10 animals in this group but one animal died from the tumor the day before autopsy.

Example 3

(Antitumor activity in the case of intravenous administration)

Under the same conditions as used in Example 2, an antitumor agent comprising IL-2 and 6-0-[10-(2,3-dimethoxy-5-methyl-1,4-benzoquinon-6-yl)decanoyl]-N-acetylmuramyl-L-valyl-D-isoglutamine methyl ester (quinonyl-MDP-66) was administered intravenously for 10 consecutive days. In this case, the antitumor effect was found to be as shown in Table 5.

TABLE 3

| Dose (mcg/mouse/day) | | Number of animals | Tumor weight (mg) Mean ± SD | Tumor weight ratio (T/C %) | Body weight gain (g) (day 7 to day 21) |
| --- | --- | --- | --- | --- | --- |
| IL-2 | Quinonyl-MDP-66 | | | | |
| Untreated control | | 15 | 3,532 ± 1,183 | | 3.0 |
| Solvent (control) | | 5 | 2,650 ± 363 | 75 | 1.7 |
| 10 | 0 | 5 | 1,999 ± 709 | 57 | 1.3 |
| 10 | 200 | 5 | 984 ± 693 | 28 | 0.3 |

Example 4

(Antitumor activity in the case of subcutaneous administration)

Under the same conditions as used in Example 1, antitumor agents comprising IL-2 and one of the two muramyldipeptides (TMD-5 or TMD-76) were administered subcutaneously for 10 consecutive days. The antitumor activity data thus obtained are shown in Table 4.

TABLE 4

| Dose (mcg/mouse/day) | | | Number of animals | Tumor weight (mg) Mean ± SD | Tumor weight ratio (T/C %) | Body weight gain (g) (day 7 to day 21) |
| --- | --- | --- | --- | --- | --- | --- |
| IL-2 | TMD-5* | TMD-76** | | | | |
| Untreated control | | | 10 | 5,747 ± 741 | | 3.3 |
| 10 | 0 | 0 | 5 | 3,072 ± 837 | 54 | 2.1 |
| 0 | 200 | 0 | 5 | 5,662 ± 1,097 | 99 | 3.0 |
| 0 | 0 | 200 | 5 | 5,550 ± 1,776 | 97 | 3.5 |
| 10 | 200 | 0 | 5 | 192 ± 171 | 3 | −0.5 |
| 10 | 0 | 200 | 5 | 1,714 ± 868 | 30 | 0.3 |

*TMD-5: N—Acetylmuramylaminoisobutyryl-D-isoglutamine
**TMD-76: 6-0-[3-(2,3-dimethoxy-5-methyl-1,4-benzoquinon-6-yl)propionyl]-N—acetyl-muramyl-L-valyl-D-isoglutamine Example 5

(Injection preparation)

| | |
| --- | --- |
| IL-2 | 10 mg |
| N—Acetylmuramyl-D-alanyl-L-isoglutamine | 200 mg |
| Lactose | 85 mg |
| HPC-L (hydroxypropylcellulose) | 5 mg |
| Total | 300 mg |

The above four materials were mixed in the above proportions and then dissolved in distilled water (1000 ml) for injection or physiological saline and, following addition of human serum albumin (HSA) in a concentration of 0.5%, the resultant solution was filtered through a membrane filter (pore diameter: 0.22 μm). The filtrate thus obtained was distributed in 1-ml portions into vials under aseptic conditions and lyophilized to give (1000 vials of) an antitumor preparation for injection. This injection preparation in each vial is to be dissolved in 1 ml of distilled water for injection at the time of use.

Example 6

(Injection preparation)

| | |
| --- | --- |
| IL-2 | 100 mg |
| N—Acetylmuramylaminoisobutyryl-D-isoglutamine | 100 mg |
| Total | 200 mg |

The above two ingredients were mixed together in the above proportions and dissolved in distilled water (1000 ml) for injection or physiological saline and, following addition of human serum albumin (HSA) in a concentration of 0.5%, the resultant solution was filtered through a membrane filter (pore diameter: 0.22 μm). The filtrate thus obtained was distributed in 1-ml portions into vials and lyophilized to give (1000 vials of) an antitumor preparation for injection. This injectable preparation in each vial is to be dissolved in 1 ml of distilled water for injection at the same time of use.

Example 7

6-0-[10-(2,3-dimethoxy-5-methyl-1,4-benzoquinon-6-yl)decanoyl-N-acetylmuramyl-L-valyl-D-isoglutamine methyl ester (quinonyl-MDP-66) (2 g) was dispersed in 100 g of squalane and the dispersion was converted to a fine-particle dispersion in a Manton-Gaulin homogenizer. In the dispersion was dissolved 50 g of HCO-50 (Nikko Chemicals, Japan). After homogeneous dissolution, a 15-g portion was weighed and used as the oil phase.

Separately, 5.6 g of d-mannitol was dissolved in 100 ml of water and the solution was used as the water phase. The aqueous phase was added to the oil phase with stirring to make up an O/W emulsion. Further treatment in the Manton-Gaulin homogenizer gave a fine-particle emulsion containing 200 mcg of the quinonyl compound per 1.2 ml. A vial was charged with 2.4 ml of this emulsion and 1 ml of an aqueous IL-2 solution having a concentration of 20 mcg/ml. After making the mixture homogeneous, the mixture was lyophilized to give an antitumor preparation. This injectable preparation is to be dissolved in distilled water for injection at the time of use.

Example 8

(Injection preparation)

| | |
|---|---|
| IL-2 (Ala-species) | 10 mg |
| N—Acetylmuramyl-D-alanyl-L-isoglutamine | 200 mg |
| Lactose | 85 mg |
| HPC-L (hydroxypropylcellulose) | 5 mg |
| Total | 300 mg |

The above four materials were mixed in the above proportions and then dissolved in distilled water (1000 ml) for injection or physiological saline and, following addition of human serum albumin (HSA) in a concentration of 0.5%, the resultant solution was filtered through a membrane filter (pore diameter: 0.22 μm). The filtrate thus obtained was distributed in 1-ml portions into vials under aseptic conditions and lyophilized to give an antitumor preparation for injection. This injectable preparation in each vial is to be dissolved in 1 ml of distilled water for injection at the time of use.

Example 9

(Injection preparation)

| | |
|---|---|
| IL-2 (Ala-species) | 100 mg |
| N—Acetylmuramylaminoisobutyryl-D-isoglutamine | 100 mg |
| Total | 200 mg |

The above two ingredients were mixed together in the above proportions and dissolved in distilled water (1000 ml) for injection or physiological saline and, following addition of human serum albumin (HSA) in a concentration of 0.5%, the resultant solution was filtered through a membrane filter (pore diameter: 0.22 μm). The filtrate thus obtained was distributed in 1-ml portions into vials and lyophilized to give 1000 vials of an antitumor preparation for injection. This injectable preparation in each vial is to be dissolved in 1 ml of distilled water for injection at the time of use.

Example 10

6-0-[10-(2,3-dimethoxy-5-methyl-1,4-benzoquinon-6-yl)decanoyl-N-acetylmuramyl-L-valyl-D-isoglutamine methyl ester (quinonyl-MDP-66) (2 g) was dispersed in 100 g of squalane and the dispersion was converted to a fine-particle dispersion in a Manton-Gaulin homogenizer. In the dispersion was dissolved 50 g of HCO-50 (Nikko Chemicals). After homogeneous dissolution, a 15-g portion was weighed and used as the oil phase. Separately, 5.6 g of d-mannitol was dissolved in 100 ml of water and the solution was used as the water phase. The aqueous phase was added to the oil phase with stirring to make up an O/W emulsion. Further treatment in the Manton-Gaulin homogenizer gave a fine-particle emulsion containing 200 mcg of the quinonyl compound per 1.2 ml. A vial was charged with 2.4 ml of this emulsion and 1 ml of an aqueous IL-2 (Ala-species) solution having a concentration of 20 mcg/ml. After making the mixture homogeneous, the mixture was lyophilized to give an antitumor preparation. This injectable preparation is to be dissolved in distilled water for injection at the time of use.

The following references, which are referred to for their disclosures at various points in this application, are incorporated herein by reference.

J. Immunol. 125, 1904(1980)
Japanes Patent Laid-open No. 60-115528
EPC Publication No. 145390
Immunobiology and Immunotherepy of Cancer, 311–330, 1978
EPC Publication No. 176299
EPC Publication No. 91539
Japanese Patent Laid-open No. 60-126088
Japanese Patent Laid-open No. 59-93093
U.S. Pat. No. 4,518,584
Japanese Patent Laid-open No. 60-226821
Japanese Patent Laid-open No. 60-205873
U.S. Pat. No. 4,101,536
Japanese Patent Laid-open No. 54-63016
Japanese Patent Laid-open No. 54-79228
EPC Publication No. 2677
Japanese Patent Laid-open No. 55-111499
U.S. Pat. No. 4,369,178

What we claim is:

1. A method for immunostimulating a warm-blooded animal, which comprises administering an effective amount of a substance having interleukin-2 activity in combination with an effective amount of a muramyl-dipeptide to said animal, wherein said interleukin-2 activity is activity to allow indefinite propagation of T cells.

2. A method as claimed in claim 1, wherein the active substances are administered to a warm-blooded animal containing at least one tumor.

3. A method as claimed in claim 1, wherein the substance having interleukin-2 activity and the muramyl-dipeptide are administered in a form of a single preparation.

4. A method as claimed in claim 1, wherein the substance having interleukin-2 activity and the muramyl-dipeptide are separately administered.

5. A method as claimed in claim 1, wherein the substance having interleukin-2 activity is a recombinant non-glycosylated human interleukin-2.

6. A method as claimed in claim 5, wherein the recombinant non-glycosylated human interleukin-2 dose not have a methionine residue at the amino teminus.

7. A method as claimed in claim 1, wherein the muramyldipeptide is a compound of the formula:

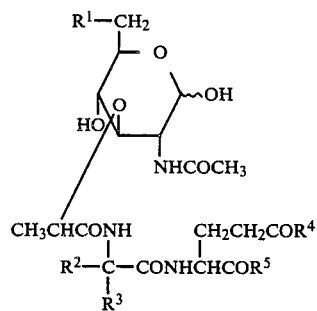

(I)

wherein $R^1$ is hydroxyl group or a $C_{2-50}$ carboxylic acid residue of the formula:

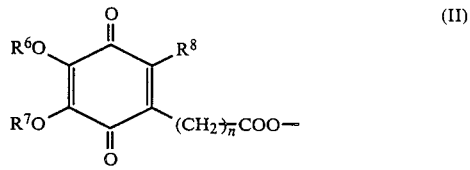

(II)

wherein $R^6$, $R^7$ and $R^8$ each dependently is a $C_{1-4}$ alkyl and n is an integer of 1 to 10, $R^2$ and $R^3$ is hydrogen or a hydroxyl-substituted or unsubstituted a $C_{1-6}$ alkyl group, $R^4$ is a hydroxyl group or a $C_{1-6}$ alkoxy group, and $R^5$ is a hydroxyl group or an amino group.

8. A method as claimed in claim 7, wherein the muramyldipeptide is N-acetylmuramyl-L-alanyl-D-isoglutamine.

9. A method as claimed in claim 7, wherein the muramyldipeptide is N-acetylmuramylaminoisobutyryl-D-isoglutamine.

10. A method as claimed in claim 7, wherein the muramyldipeptide is 6-0-[3-(2,3-dimethoxy-5-methyl-1,4-benzoquinon-6-yl)propionyl]-N-acetyl-muramyl-L-valyl-D-isoglutamine.

11. A method as claimed in claim 7, wherein the muramyldipeptide is
6-0-[10-(2,3-dimethoxy-5-methyl-1,4-benzoquinon-6-yl)decanoyl]-N-acetylmuramyl-L-valyl-D-isoglutamine methyl ester.

* * * * *